United States Patent
Miki et al.

(10) Patent No.: US 8,669,395 B2
(45) Date of Patent: Mar. 11, 2014

(54) OPTICALLY ACTIVE 4-AMINO-3-(4-CHLOROPHENYL)BUTANOIC ACID

(75) Inventors: Takashi Miki, Toyonaka (JP); Masahiro Takeda, Nishinomiya (JP); Tetsuro Yamazaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 300 days.

(21) Appl. No.: 12/966,288

(22) Filed: Dec. 13, 2010

(65) Prior Publication Data

US 2011/0152572 A1 Jun. 23, 2011

(30) Foreign Application Priority Data

Dec. 17, 2009 (JP) ................................ 2009-286044

(51) Int. Cl.
*C07C 229/00* (2006.01)
(52) U.S. Cl.
USPC ........................................................ 562/449
(58) Field of Classification Search
None
See application file for complete search history.

(56) References Cited

U.S. PATENT DOCUMENTS

| 7,354,954 B1 | 4/2008 | Meythaler et al. |
| 2006/0161006 A1 | 7/2006 | Takemoto |
| 2009/0137819 A1 | 5/2009 | Yasuoka et al. |

FOREIGN PATENT DOCUMENTS

JP 45-016692 6/1970

OTHER PUBLICATIONS

Caira, et al. "Optical resolution of baclofen *via* diastereomeric salt pair formation between 3-(*p*-chlorophenyl)glutaramic acid and (*S*)-(−)-α-phenylethylamine" J. Chem. Soc. Perkin Trans. 2, 1997, pp. 763-768.
Chenevert, et al. "Chemoenzymatic Synthesis of Both Enantiomers of Baclofen" Tetrahedron Letters, 1991, vol. 32, No. 34, pp. 4249-4250.
Council of Europe 2000: European Pharmacopoeia 5th ed., 1050-1051.
Langlois, et al. "Enantioselective Syntheses of (*R*)-3-Phenyl GABA, (*R*)-Baclofen and 4-Arylpyrrolidin-2-ones" Tetrahedron, 1996, vol. 52, No. 48, pp. 15117-15126.
Mirza, et al. "Solid-State Properties and Relationship between Anhydrate and Monohydrate of Baclofen" Journal of Pharmaceutical Sciences, Sep. 2007, vol. 96, No. 9, pp. 2399-2408.
Okino, et al. "Enantio-and Diastereoselective Michael Reaction of 1,3-Dicarbonyl Compounds to Nitroolefins Catalyzed by a Bifunctional Thiourea" J. Am. Chem. Soc., 2005, vol. 127, pp. 119-125.
Olpe, et al. The Biological Activity of d-And l-Baclofen (LIORESAL ®), European Journal of Pharmacology, 1978, vol. 52, pp. 133-136.
Resende, et al. "An efficient synthesis of (*R*)-(−)-baclofen" Tetrahedron: Asymmetry, 1999, vol. 10, pp. 2113-2118.
Shishido, et al. "Lipase-mediated asymmetric acetylation of prochiral diols directed towards total syntheses of biologically active molecules" Journal of Molecular Catalysis B: Enzymatic, 1998, vol. 5, pp. 183-186.
Wang, et al. "Highly enantioselective biotransformations of 2-aryl-4-pentenenitriles, a novel chemoenzymatic approach to (*R*)-(−)-baclofen" Tetrahedron Letters, 2002, vol. 43, pp. 6617-6620.
Yoshihashi, et al. "Application of Isothermal Microcalorimetry for Stability Evaluation of Solid Dosage Form" Netsu Sokutei, 2004, vol. 31, No. 2, pp. 80-86.
Mino R. Caira, "Crystalline Polymorphism of Organic Compounds", Topics in Current Chemistry, vol. 198, XP-001156954, 1998, pp. 163-208.
European Search Report issued in corresponding EP application 10194532.7, dated Jun. 6, 2011, 5 pages.

*Primary Examiner* — Sudhakar Katakam
(74) *Attorney, Agent, or Firm* — Foley & Lardner LLP

(57) ABSTRACT

Provided is a new crystal A of optically active 4-amino-3-(4-chlorophenyl)butanoic acid which is far better in stability, and a process for producing the crystal and a process for producing the crystal A comprising a step of heating the following crystal B in water having a pH of 3 to 9:

crystal A:
a crystal of optically active 4-amino-3-(4-chlorophenyl) butanoic acid which has diffraction peaks within the range of a diffraction angle 2θ of 8.7 to 9.4°, within that of 2θ of 12.2 to 12.8°, and within that of 2θ of 24.8 to 25.4° in a powder X-ray diffraction measurement of the crystal by use of the Cu—Kα wavelength; and crystal B:
a crystal of optically active 4-amino-3-(4-chlorophenyl) butanoic acid which has diffraction peaks within the range of a diffraction angle 2θ of 20.8 to 21.4°, within that of 2θ of 26.7 to 27.3°, and within that of 2θ of 29.7 to 30.3° in a powder X-ray diffraction measurement of the crystal by use of the Cu—Kα wavelength.

8 Claims, 4 Drawing Sheets

OPTICALLY ACTIVE 4-AMINO-3-(4-CHLOROPHENYL)BUTANOIC ACID

TECHNICAL FIELD

The present invention relates to a new crystal of optically active 4-amino-3-(4-chlorophenyl) butanoic acid, and a process for producing the crystal.

BACKGROUND ART

Optically active baclofen [4-amino-3-(4-chlorophenyl) butanoic acid] is a raw material of medicine, or an intermediate thereof (see, for example, U.S. Pat. No. 7,354,954).

As a process for producing optically active 4-amino-3-(4-chlorophenyl)butanoic acid, known is, for example, a process described in US2009/0137819, or a process described in Journal of the Chemical Society, Perkin Transactions 2, 1997, pp. 763-768.

In the process described in US2009/0137819, a crystal of optically active 4-amino-3-(4-chlorophenyl)butanoic acid is yielded by a method of adding an aqueous solution of sodium hydroxide into an aqueous solution of a hydrochloride salt of optically active 4-amino-3-(4-chlorophenyl)butanoic acid to attain neutralizing crystallization, or in the process of Journal of the Chemical Society, Perkin Transactions 2, 1997, pp. 763-768, the same salt is yielded by a method of adding diluted hydrochloric acid to an aqueous sodium hydroxide solution of optically active 4-amino-3-(4-chlorophenyl) butanoic acid to attain neutralizing crystallization. The journal also states that the crystal is further heated in methanol. However, these literatures never disclose that polytype crystals of optically active 4-amino-3-(4-chlorophenyl)butanoic acid exist.

SUMMARY OF THE INVENTION

The present invention provides a new crystal of optically active 4-amino-3-(4-chlorophenyl)butanoic acid which is better in stability than known 4-amino-3-(4-chlorophenyl) butanoic acid.

That is, the present invention provides the following crystal A:

crystal A:
a crystal of optically active 4-amino-3-(4-chlorophenyl) butanoic acid which has diffraction peaks within the range of a diffraction angle 2θ of 8.7 to 9.4°, within the range of a diffraction angle 2θ of 12.2 to 12.8°, and within the range of a diffraction angle 2θ of 24.8 to 25.4° in a powder X-ray diffraction measurement of the crystal by use of the Cu—Kα wavelength; and
a process for producing the crystal A comprising a step of heating the following crystal B in water having a pH of 3 to 9.

crystal B:
a crystal of optically active 4-amino-3-(4-chlorophenyl) butanoic acid which has diffraction peaks within the range of a diffraction angle 2θ of 20.8 to 21.4°, within the range of a diffraction angle 2θ of 26.7 to 27.3°, and within the range of a diffraction angle 2θ of 29.7 to 30.3° in a powder X-ray diffraction measurement of the crystal by use of the Cu—Kα wavelength.

DETAILED DESCRIPTION OF THE INVENTION

A description is first made about a crystal of optically active 4-amino-3-(4-chlorophenyl)butanoic acid which has diffraction peaks within the range of a diffraction angle 2θ of 8.7 to 9.4°, within the range of a diffraction angle 2θ of 12.2 to 12.8°, and within the range of a diffraction angle 2θ of 24.8 to 25.4° in a powder X-ray diffraction measurement thereof by use of the Cu—Kα wavelength. Hereinafter, the crystal may be referred to as "crystal A of optically active 4-amino-3-(4-chlorophenyl)butanoic acid" or merely as "crystal A".

In the invention, the wording "(some compound) has diffraction peaks" means that when the peak intensity of the strongest diffraction peak thereof is regarded as 100%, the compound has peaks the intensities (relative intensity) of which are 3% or more. The wording "(some compound) does not substantially have any diffraction peak" means that when the peak intensity of the strongest diffraction peak thereof is regarded as 100%, the compound has no peak the intensities (relative intensity) of which are 3% or more.

Figure 1:
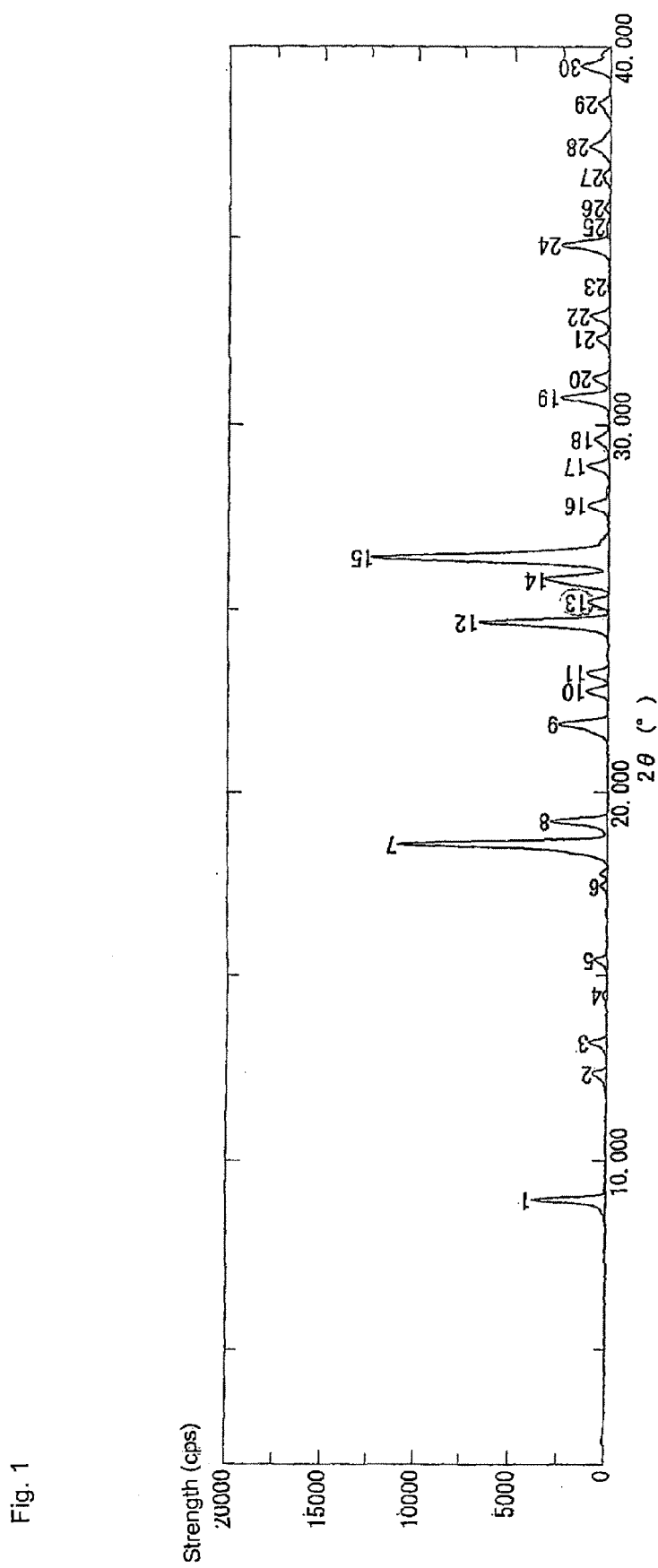
FIG. 1 shows a typical X-ray diffraction pattern of a crystal of optically active 4-amino-3-(4-chlorophenyl) butanoic acid which has diffraction peaks within the range of a diffraction angle 2θ of 8.7 to 9.4°, within the range of a diffraction angle 2θ of 12.2 to 12.8°, and within the range of a diffraction angle 2θ of 24.8 to 25.4° in a powder X-ray diffraction measurement thereof by use of the Cu—Kα wavelength.

A typical X-ray diffraction pattern in a X-ray diffraction measurement of crystal A by use of the Cu—Kα wavelength is shown in FIG. 1. In Table 1 are shown the diffraction angles 2θ at which the diffraction peaks which crystal A has in the X-ray diffraction pattern shown in FIG. 1 are given, and the relative intensities of the diffraction peaks.

TABLE 1

| No | Diffraction angle 2θ (°) | Relative intensity (%) |
|---|---|---|
| 1 | 8.9 | 32 |
| 2 | 12.3 | 6 |
| 3 | 13.2 | 8 |
| 4 | — | <3 |
| 5 | 15.4 | 6 |
| 6 | 17.4 | 3 |
| 7 | 18.6 | 90 |
| 8 | 19.2 | 25 |
| 9 | 21.9 | 22 |
| 10 | 22.8 | 10 |
| 11 | 23.3 | 10 |
| 12 | 24.6 | 55 |
| 13 | 25.2 | 9 |
| 14 | 25.8 | 26 |
| 15 | 26.4 | 100 |
| 16 | 27.8 | 10 |
| 17 | 28.9 | 10 |
| 18 | 29.6 | 7 |
| 19 | 30.7 | 22 |

TABLE 1-continued

| No | Diffraction angle 2θ (°) | Relative intensity (%) |
|---|---|---|
| 20 | 31.2 | 8 |
| 21 | 32.3 | 6 |
| 22 | 32.9 | 9 |
| 23 |  | <3 |
| 24 | 34.8 | 21 |
| 25 |  | <3 |
| 26 | 35.8 | 3 |
| 27 | 36.6 | 3 |
| 28 | 37.4 | 10 |
| 29 | 38.5 | 6 |
| 30 | 39.5 | 13 |

As shown in Table 1, crystal A does not substantially have any diffraction peak within the range of a diffraction angle 2θ of 20.8 to 21.4°, within the range of a diffraction angle 2θ of 26.7 to 27.3°, nor within the range of a diffraction angle 2θ of 29.7 to 30.3° in the powder X-ray diffraction measurement thereof by use of the Cu—Kα wavelength.

By contrast, a crystal of optically active 4-amino-3-(4-chlorophenyl)butanoic acid which has diffraction peaks within the range of a diffraction angle 2θ of 20.8 to 21.4°, within the range of a diffraction angle 2θ of 26.7 to 27.3°, and within the range of a diffraction angle 2θ of 29.7 to 30.3° in a powder X-ray diffraction measurement thereof by use of the Cu—Kα wavelength may be referred to as "crystal B of optically active 4-amino-3-(4-chlorophenyl)butanoic acid, or merely as "crystal B".

Figure 2:
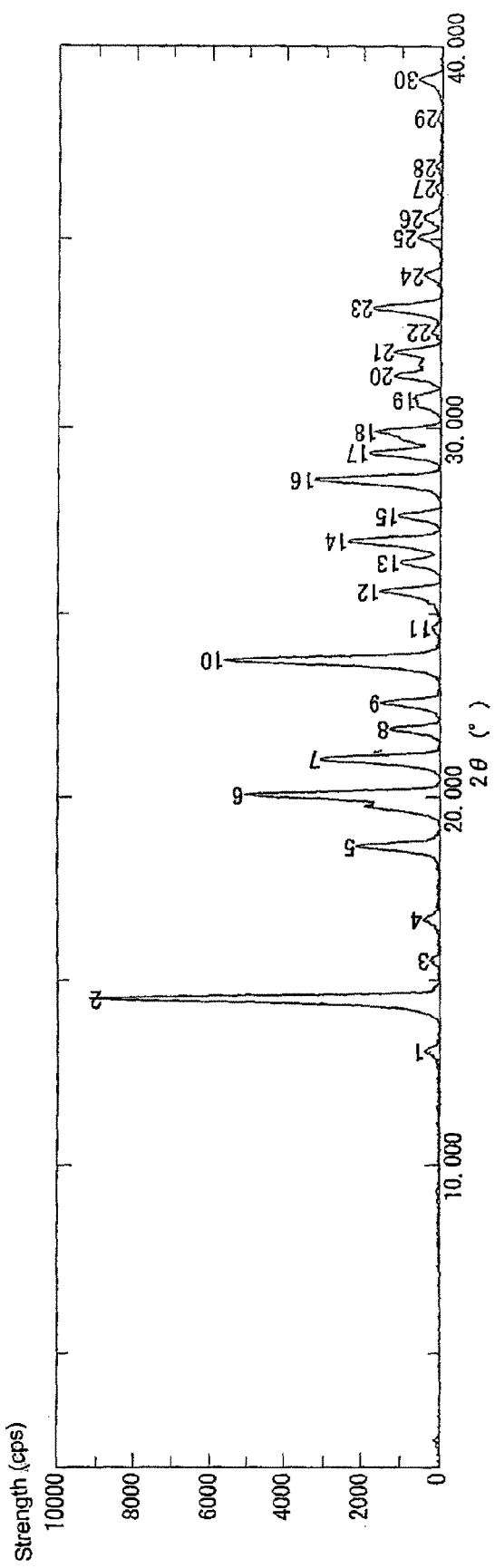
FIG. 2 shows a typical X-ray diffraction pattern of a crystal of optically active 4-amino-3-(4-chlorophenyl) butanoic acid which has diffraction peaks within the range of a diffraction angle 2θ of 20.8 to 21.4°, within the range of a diffraction angle 2θ of 26.7 to 27.3°, and within the range of a diffraction angle 2θ of 29.7 to 30.3° in a powder X-ray diffraction measurement thereof by use of the Cu—Kα wavelength.
Figure 3:
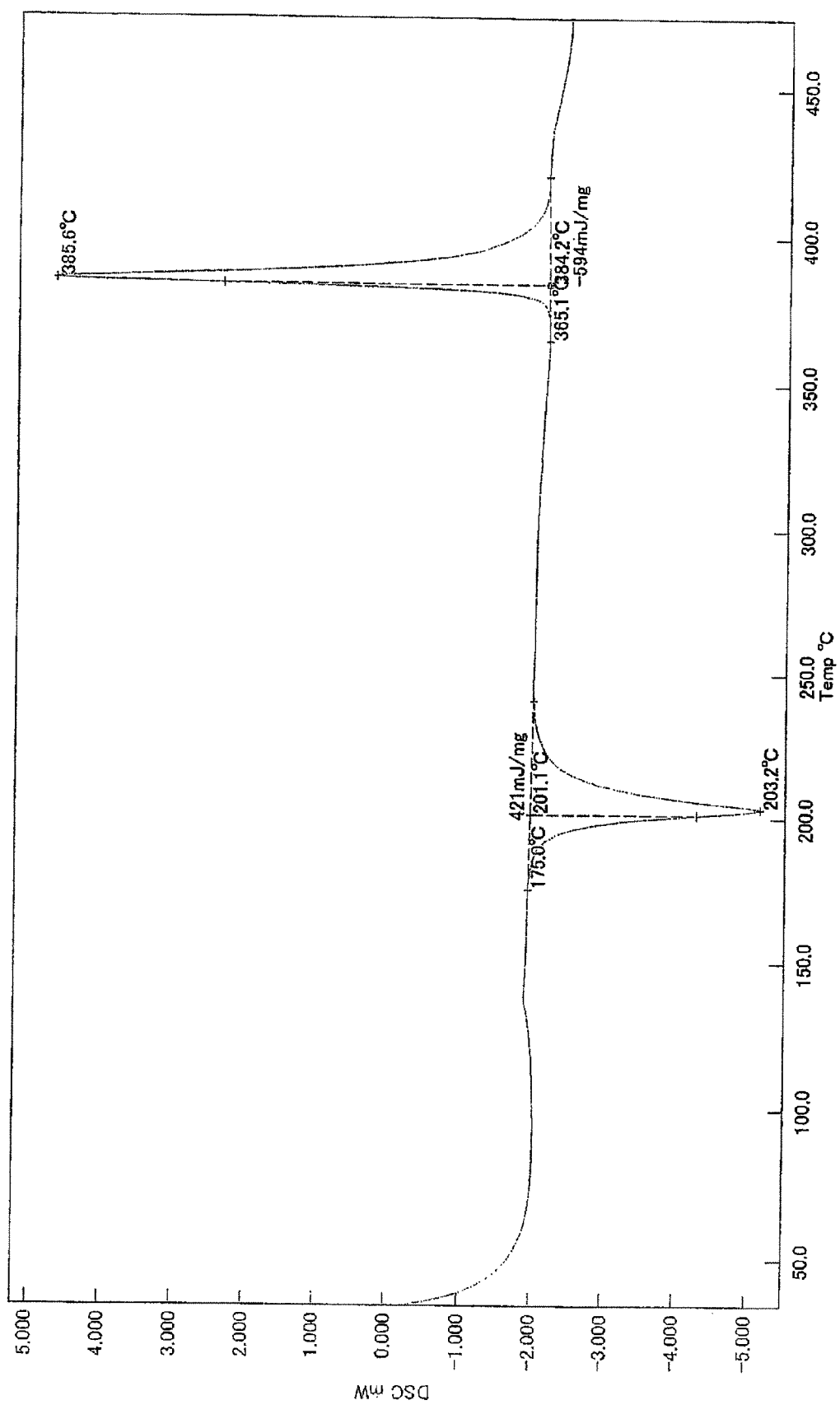
FIG. 3 shows a chart of a differential scanning calorimetry of a crystal yielded according to the same process in Example 1.
Figure 4:
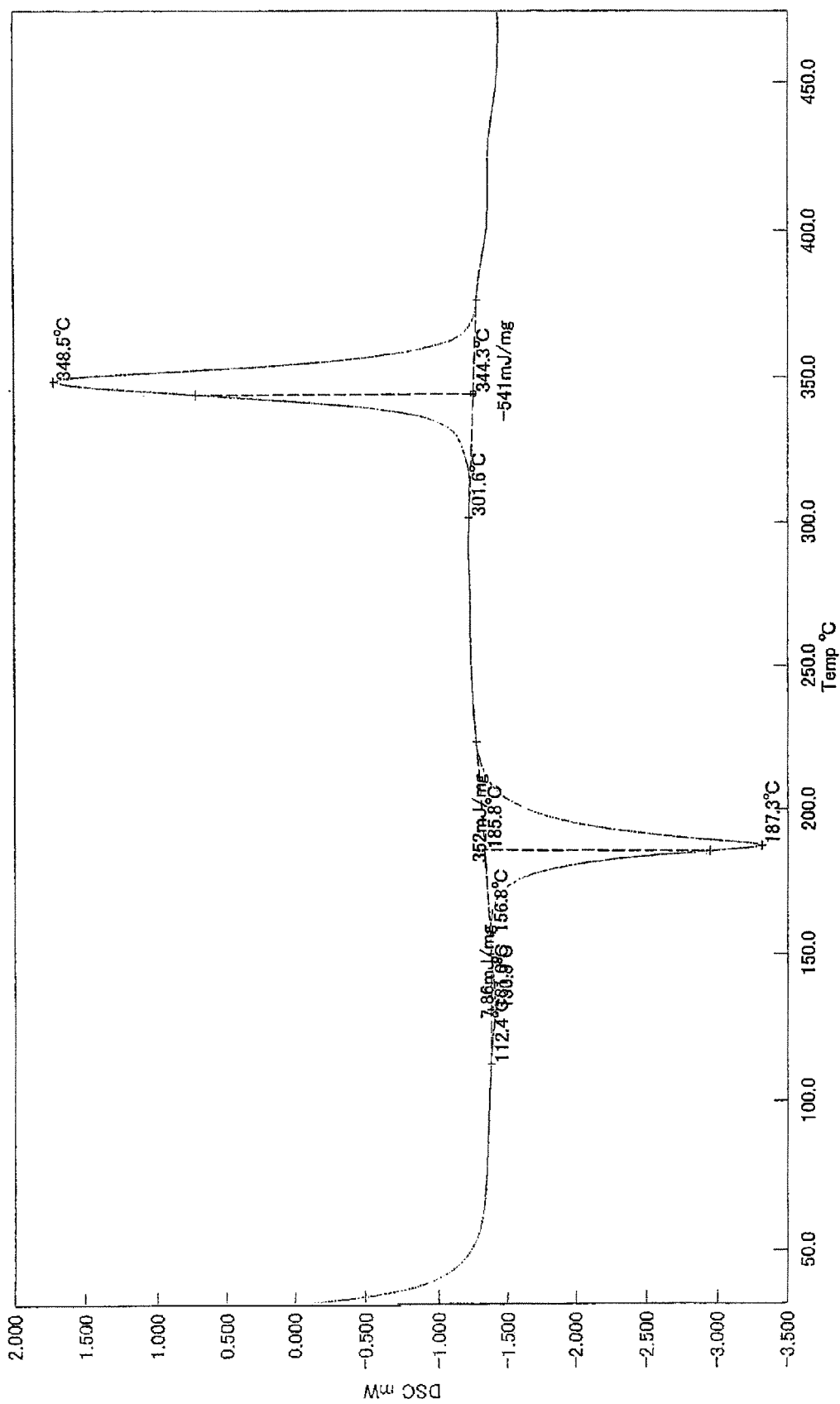
FIG. 4 shows a chart of a differential scanning calorimetry of a crystal yielded according to the same process in Comparative Example 1.

A typical X-ray diffraction pattern in a X-ray diffraction measurement of crystal B by use of the Cu—Kα wavelength is shown in FIG. 2. In Table 2 are shown the diffraction angles 2θ at which the diffraction peaks which crystal B has in the X-ray diffraction pattern shown in FIG. 2 are given, and the relative intensities of the diffraction peaks.

TABLE 2

| No | Diffraction angle 2θ (°) | Relative intensity (%) |
|---|---|---|
| 1 | 13.1 | 5 |
| 2 | 14.5 | 100 |
| 3 | 15.5 | 3 |
| 4 | 16.7 | 5 |
| 5 | 18.6 | 25 |
| 6 | 20.1 | 58 |
| 7 | 21.0 | 36 |
| 8 | 21.9 | 15 |
| 9 | 22.6 | 18 |
| 10 | 23.7 | 64 |
| 11 | 24.6 | 3 |
| 12 | 25.6 | 18 |
| 13 | 26.4 | 12 |
| 14 | 27.0 | 27 |
| 15 | 27.6 | 12 |
| 16 | 28.6 | 37 |
| 17 | 29.3 | 21 |
| 18 | 29.9 | 19 |
| 19 | 30.7 | 8 |
| 20 | 31.4 | 14 |
| 21 | 32.0 | 14 |
| 22 | 32.6 | 3 |
| 23 | 33.2 | 20 |
| 24 | 34.0 | 5 |
| 25 | 35.0 | 8 |
| 26 | 35.6 | 6 |
| 27 |  | <3 |
| 28 | — | <3 |
| 29 | 39.2 | 7 |

As shown in Table 2, crystal B does not substantially have any diffraction peak within the range of a diffraction angle 2θ of 8.7 to 9.4°, within the range of a diffraction angle 2θ of 12.2 to 12.8°, nor within the range of a diffraction angle 2θ of 24.8 to 25.4° in the powder X-ray diffraction measurement thereof by use of the Cu—Kα wavelength.

As described above, powder X-ray diffraction measurement by use of the Cu—Kα wavelength makes it possible to distinguish crystal A and crystal B evidently from each other.

X-ray diffraction measurement by use of the Cu—Kα wavelength can be made using a pulverized crystal as a sample and, for example, a goniometer manufactured by Rigaku Corp., Mini Flex II, under the following conditions:
 X-ray: Cu/30 kV/15 mA,
 filter: Kβ filter,
 divergent slit: 1.25°,
 light receiving slit: 0.3 mm,
 scattering slit: 1.25°,
 sampling width: 0.02°,
 scanning range: 2.00 to 40.00°,
 number of times of integration (or multiplication): 1,
 scanning speed: 2.0°/minute,
 scanning axis: 2θ/θ, and
 θ offset: 0°.

When the differential scanning calorie (DSC), of crystal A is measured, an endothermic peak is exhibited in the range of 200 to 210° C. while an exothermic peak is exhibited in the range of 370 to 390° C. However, when the differential scanning calorie of crystal B is measured, an endothermic peak is exhibited in the range of 180 to 190° C. while an exothermic peak is exhibited in the range of 345 to 365° C. As described herein, DSC measurement also makes it possible to distinguish crystal A and crystal B evidently from each other.

About the DSC measurement, for example, a differential scanning calorimeter of an EXTER 6000 type, manufactured by SII Nano Technology Inc., is used to make it possible to make the measurement under the following conditions:
 measuring temperature range: 25 to 500° C.,
 temperature-raising rate: 10° C./minute,
 container: air-tightly closed SUS,
 sample amount: about 0.4 to 0.7 mg,
 reference: α-alumina having a weight of about 0.6 mg, and
 atmospheric gas flow rate: dried nitrogen, about 70 mL/minute.

Since crystal A has a higher endothermic peak and a higher exothermic peak than crystal B in the DSC measurement thereof, crystal A is far better in thermal stability than crystal B. Moreover, it is considered that crystal A is far better also in storage stability than crystal B (see, for example, "Evaluation of the Stability of Solid Medicine, and Application of Micro-Calorimeter thereto", Netsu Sokutei, vol. 31, No. 2, pp. 80-86).

The solubility of crystal A in 100 g of water ranges from 0.7 to 1.1 g (0.9±0.2 g) at 25° C. On the other hand, that of crystal B in 100 g of water ranges from 1.8 to 2.2 g (2.0±0.2 g) at 25° C. As described herein, measurement of the solubilities thereof in water also makes it possible to distinguish crystal A and crystal B evidently from each other.

When crystal A taken out from a mixture containing water is dried at 50° C. under a reduced pressure, the content by percentage of water remaining in crystal A is, for example, less than 0.5%, or is, for example, less than 0.2%. On the other hand, when crystal B taken out from a mixture containing water is dried at 50° C. under a reduced pressure, the content by percentage of water remaining in crystal B is, for example, within the range of from 0.5 to 2%. These water contents by percentage can each be measured by use of a Karl Fisher moisture titrator. Crystal A is more easily dried than crystal B.

Optically active 4-amino-3-(4-chlorophenyl)butanoic acid which constitutes crystal A can be (S)-4-amino-3-(4-chlorophenyl)butanoic acid or (R)-4-amino-3-(4-chlorophenyl) butanoic acid.

The chemical purity of the optically active 4-amino-3-(4-chlorophenyl)butanoic acid which constitutes crystal A is preferably 95% or more by weight of crystal A, more preferably 98% or more by weight thereof, even more preferably 99% or more thereof. The enantiomer excess (percentage) thereof is preferably 95% or more, more preferably 98% or more, even more preferably 99% or more. About the optically active 4-amino-3-(4-chlorophenyl)butanoic acid, (S)-4-amino-3-(4-chlorophenyl)butanoic acid may be excessive, or (R)-4-amino-3-(4-chlorophenyl)butanoic acid may be excessive.

The following will describe a process for producing crystal A. This producing process includes the step of heating crystal B in water having a pH of 3 to 9. When crystal B is heated in water having a pH of 3 to 9, crystal B can be converted to crystal A.

In the present process, crystal A of (S)-4-amino-3-(4-chlorophenyl)butanoic acid is obtained when crystal B of (S)-4-amino-3-(4-chlorophenyl)butanoic acid is used. When crystal B of (R)-4-amino-3-(4-chlorophenyl)butanoic acid is used, crystal A of (R)-4-amino-3-(4-chlorophenyl)butanoic acid is obtained.

The chemical purity of the optically active 4-amino-3-(4-chlorophenyl)butanoic acid which constitutes crystal B is preferably 95% or more by weight of crystal B, more preferably 98% or more by weight thereof, even more preferably 99% or more by weight thereof. The enantiomer excess thereof is preferably 95% or more, more preferably 98% or more, even more preferably 99% or more.

Crystal B may be produced by a known process described in US2009/0137819 or Journal of the Chemical Society, Perkin Transactions 2, 1997, pp. 763-768, or a process to which the known process is applied. Specific examples thereof include a process of mixing an aqueous solution of a hydrochloride salt of optically active 4-amino-3-(4-chlorophenyl) butanoic acid with an inorganic base to attain neutralizing crystallization, a process of mixing an aqueous sodium hydroxide solution of optically active 4-amino-3-(4-chlorophenyl) butanoic acid with a mineral acid to attain neutralizing crystallization, and a process of mixing an aqueous sodium hydroxide solution of optically active 4-amino-3-(4-chlorophenyl) butanoic acid with a mineral acid to attain neutralizing crystallization, and then heating the resultant crystal in an alcohol solvent such as methanol. Preferred is the process of mixing an aqueous solution of a hydrochloride salt of optically active 4-amino-3-(4-chlorophenyl)butanoic acid with an inorganic base to attain neutralizing crystallization. In these processes, treatment with activated carbon may be conducted before the aqueous solution is mixed with the inorganic base or mineral acid to attain the neutralizing crystallization.

The amount of water in the aqueous solution of the hydrochloride salt of optically active 4-amino-3-(4-chlorophenyl) butanoic acid is preferably from 0.5 to 20 parts by weight per part by weight of the hydrochloride salt of optically active 4-amino-3-(4-chlorophenyl)butanoic acid, more preferably from 1 to 5 parts by weight per part by weight thereof.

The amount of water in the aqueous sodium hydroxide solution of optically active 4-amino-3-(4-chlorophenyl)butanoic acid is preferably from 0.5 to 20 parts by weight per part by weight of optically active 4-amino-3-(4-chlorophenyl) butanoic acid, more preferably from 1 to 10 parts by weight per part by weight thereof.

The neutralizing crystallization may be conducted by adjusting the pH preferably into the range of 3 to 9, more preferably into that of 4 to 8.

Examples of the inorganic base used when the pH is adjusted include alkali metal hydroxides, such as lithium hydroxide, sodium hydroxide and potassium hydroxide, alkali metal carbonates such as sodium carbonate and potassium carbonate, and alkali metal hydrogencarbonates such as sodium hydrogencarbonate. Preferred are alkali metal hydroxides, and more preferred is sodium hydroxide. The inorganic base can be a single species thereof or a mixture of two or more species. The inorganic base may be used in the state that the base is mixed with water.

Examples of the mineral used to adjust the pH include hydrochloric acid, sulfuric acid, and phosphoric acid. Hydrochloric acid is preferred. About the mineral acid, a single species thereof may be used, or two or more thereof may be used. The mineral acid may be used in the state of being mixed with water.

The temperature when the pH is adjusted ranges preferably from 0 to 40° C., more preferably from 10 to 30° C. in order to improve the yield of crystal B.

The present process may be conducted after the mixture yielded by the neutralizing crystallization is subjected to a solid-liquid separating treatment such as filtration or decantation, or without taking out crystal B from the mixture yielded by the neutralizing crystallization. The solid-liquid separating treatment is preferably filtration. The temperature in the solid-liquid separating treatment ranges preferably from 0 to 40° C., more preferably from 10 to 30° C. Crystal B taken out may be subjected to drying treatment after it is subjected to washing treatment with water or the like, or without being subjected to any washing treatment. The drying treatment is conducted under normal pressure or reduced pressure preferably at a temperature ranging from 20 to 80° C.

It is preferred from the viewpoint of working efficiency that the present process is conducted without taking out crystal B from the mixture yielded by the neutralizing crystallization.

About crystal B, the enantiomer excess of optically active 4-amino-3-(4-chlorophenyl)butanoic acid therein can be improved by subjecting the crystal B to purifying treatment with an organic acid solution in water. The organic acid solution in water is prepared by dissolving an organic acid into water.

Examples of the organic acid used in the purifying treatment include carboxylic acids such as formic acid, acetic acid, propionic acid, succinic acid, fumaric acid, lactic acid, malic acid, tartaric acid, citric acid, and other carboxylic acids. Preferable organic acid is acetic acid.

The concentration of the organic acid in the organic acid solution in water is preferably from 0.2 to 3% by weight, more preferably from 0.5 to 2% by weight. If the concentration of the organic acid in the organic acid solution in water is less than 0.2% by weight, the effect of the purification tends to decline. If the concentration is more than 3% by weight, the yield tends to lower. The amount of water used in the purifying treatment ranges preferably from 1 to 8 parts by weight per part by weight of crystal B supplied to the purifying treatment.

The purifying treatment of crystal B can be conducted, specifically, by a method of suspending crystal B into the organic acid solution in water, a method of mixing an aqueous solution of a hydrochloride salt of optically active 4-amino-3-(4-chlorophenyl)butanoic acid with an inorganic acid to attain neutralizing crystallization, and then adding the organic acid thereto, a method of mixing an aqueous sodium hydroxide solution of optically active 4-amino-3-(4-chlorophenyl)butanoic acid with a mineral acid to attain neutralizing crystallization, and adding the organic acid thereto, or some other method. The temperature for the purifying treatment ranges preferably from 0 to 40° C., more preferably from 20 to 30° C. The period for the purifying treatment ranges, for example, from 30 minutes to 10 hours.

After the mixture containing crystal B subjected to the purifying treatment is subjected to a solid-liquid separating treatment such as filtration or decantation, thereby taking out crystal B, the present process may be performed. Alternatively, without taking out crystal B subjected to the purifying treatment from the mixture, the present process may be performed. The solid-liquid separating treatment is preferably filtration. The temperature in the solid-liquid separating treatment ranges preferably from 0 to 40° C., more preferably from 10 to 30° C. Crystal B taken out may be subjected to drying treatment after being subjected to washing treatment with water or the like, or without being subjected to washing treatment. The drying treatment is conducted under normal pressure or reduced pressure preferably at a temperature ranging from 20 to 80° C.

It is preferred from the viewpoint of working efficiency to perform the present process without taking out, from the mixture, crystal B subjected to the purifying treatment.

The amount of water in the present process ranges preferably from 1 to 20 parts by weight, more preferably from 2 to 10 parts by weight per part by weight of crystal B. Water may be used alone, or may be used in the state of being mixed with an organic solvent miscible with water. Examples of the organic solvent miscible with water include alcohol solvents having 3 or less carbon atoms, such as methanol, ethanol, propanol and 2-propanol, cyclic ethers such as tetrahydrofuran and dioxane, acetonitrile, acetone, and ethylene glycol monomethyl ether. The organic solvent miscible with water can be a single species thereof or a mixture of two or more species thereof. When the organic solvent miscible with water is used, the use amount of the organic solvent is preferably less than 1 part by weight per part by weight of water.

The pH of water in the present process ranges from 3 to 9. In order to improve the yield, the pH ranges preferably from 4 to 8.

The adjustment of the pH can be attained by the addition of an acid and/or a base. Examples of the acid include carboxylic acids such as formic acid, acetic acid, propionic acid and tartaric acid, sulfonic acids such as methanesulfonic acid, and inorganic acids such as hydrochloric acid, sulfuric acid and phosphoric acid. Examples of the base include alkali metal hydroxides such as sodium hydroxide and potassium hydroxide, alkali metal carbonates such as sodium carbonate and potassium carbonate, and alkali metal hydrogencarbonates such as sodium hydrogencarbonate and potassium hydrogencarbonate. Sodium chloride, sodium acetate or some other salt may be present.

As a seed crystal, crystal A may be added. The amount of the seed crystal to be added ranges preferably from 0.0005 to 0.2 part by weight, more preferably from 0.001 to 0.1 part by weight per part by weight of crystal B.

The heating temperature ranges preferably from 40 to 100° C., more preferably from 50 to 90° C. The heating period ranges preferably from 5 minutes to 24 hours, more preferably from 10 minutes to 15 hours.

The present process is performed by, for example, a method of heating a mixture of crystal B and water to a predetermined temperature, and then adding an acid and/or a base thereto, thereby adjusting water in the resultant mixture into a pH of 3 to 9, or a method of adding an acid and/or a base to a mixture of crystal B and water, thereby adjusting water in the resultant mixture into a pH of 3 to 9, and then heating the mixture.

The mixture yielded through the present process is optionally subjected to cooling treatment, and then subjected to a solid-liquid separating treatment such as filtration or decantation, whereby crystal A can be taken out. The solid-liquid separating treatment is preferably filtration. The temperature in the solid-liquid separating treatment may be selected from the range from the solidifying point of water to the boiling point thereof. The temperature ranges preferably from 0 to 70° C., more preferably from 10 to 60° C. Crystal A taken out may be subjected to washing treatment. In the washing treatment, for example, water may be used. Crystal A taken out may be subjected to drying treatment after being subjected to the washing treatment with water or the like, or without being subjected to washing treatment. The drying treatment is conducted under normal pressure or reduced pressure preferably at a temperature in the range of 20 to 80° C.

EXAMPLES

Hereinafter, the invention will be described in more detail by the following examples.

Synthesis Example 1

Synthesis of 4-chloro-β-nitrostyrene

To 1066.8 g of acetic acid were added 200.14 g (1.356 mol) of 4-chlorobenzaldehyde, and 153.4 g (1.429 mol) of benzylamine, and the added components were dissolved in the acid. This solution was heated to 78° C., and 325.7 g (5.336 mol) of nitromethane was dropwise added thereto at 78 to 80° C. over 2 hours and 50 minutes. Thereafter, the solution was stirred at about 79° C. for 40 minutes. Next, 1016 g of water was dropwise added thereto at about 50° C. over 2 hours and 25 minutes. The mixture was cooled to about 10° C. and was stirred at 6 to 10° C. for 1 hour and 50 minutes. The obtained crystals were filtered, and washed with 1016.2 g of water. The wet crystals were dissolved into 572.8 g of toluene at about 50° C. The resultant was separated into two phases, and the water phase thereof was removed. The remaining phase was washed with 330.8 g of water. By HPLC, 803.24 g of the toluene phase was analyzed. As a result, the phase contained 253.8 g of 4-chloro-β-nitrostyrene. The yield thereof was 97.1%.

Synthesis Example 2

Synthesis of ethyl (S)-2-ethoxycarbonyl-4-nitro-3-phenyllactate

In an atmosphere of nitrogen, 3730 g of a solution containing 4-chloro-β-nitrostyrene (1492 g, 8.1 mol) in toluene was mixed with a solution obtained by dissolving 34 g (0.0082 mol) of (R,R)-trans-1-[3,5-bis(trifluoromethyl)phenyl]-3-[2-(N,N-dimethylamino)cyclohexyl]thiourea, which was produced by the method described in US2006/0161006, into 100 g of toluene. To the resultant mixture, 3905 g (24.4 mol) of diethyl malonate was added at about 20° C. After 24 hours, the reaction mixture was concentrated under reduced pressure to yield 5648 g of a solution containing 2598 g of ethyl (S)-2-ethoxycarbonyl-4-nitro-3-phenyllactate in toluene. The yield was 93%. The resultant solution in toluene was partially taken out, and then it was verified by HPLC that ethyl (S)-2-ethoxycarbonyl-4-nitro-3-phenyllactate was yielded.

Synthesis Example 3

Synthesis of ethyl (3S,4R)-4-(4-chlorophenyl)-2-oxopyrrolidine-3-carbonate

In an atmosphere of nitrogen, to 7144 g of 2-propanol were added 5646 g of a solution containing 2597 g (7.55 mol) of ethyl (S)-2-ethoxycarbonyl-4-nitro-3-phenyllactate, yielded in Synthesis Example 2, in toluene, and 519 g of developed nickel, PL9T (manufactured by Kawaken Fine Chemicals Co., Ltd.), so as to cause the reactive components to react with each other under a hydrogen pressure of 0.5 MPa (gauge pressure) at about 70° C. After the end of the reaction, the nickel catalyst was filtrated off, and the filtrate was concentrated under reduced pressure. To the concentrated product was added 3392 g of 1,2-dichlorobenzene. This solution was analyzed by HPLC. As a result, the solution contained 1618 g of ethyl (3S,4R)-4-(4-chlorophenyl)-2-oxopyrrolidine-3-carbonate.

Synthesis Example 4

Synthesis of a hydrochloride salt of (R)-4-amino-3-(4-chlorophenyl)butanoic acid To 7035 g of a solution containing 1618 g of ethyl (3S,4R)-4-(4-chlorophenyl)-2-oxopyrrolidine-3-carbonate, yielded in Synthesis Example 3, in 1,2-dichlorobenzene were added 2425 g of water and 3236 g of 35% hydrochloric acid, and then the solution was stirred at about 100° C. for 24 hours. The resultant reaction mixture was cooled, and then separated into two phases. To the water phase was added 3392 g of 1,2-dichlorobenzene to wash the phase, and then the solution was again separated into two phases. The resultant water phase was heated and refluxed, and then thereto was added 8417 g of toluene at 70 to 90° C. Until the temperature of the inside solution turned to 110° C., the solution was azeotropically dehydrated to distill off water. Next, toluene was distilled off until the inside temperature turned to 111° C. Thereto were added 143 g of water and 2494 g of acetonitrile, and the mixture was cooled. The solution was then stirred at about 20° C. for 1 hour. The mixture was filtrated, washed with a mixed liquid of 63 g of water and 2494 g of acetonitrile, and then dried. This way gave 1361 g of a hydrochloride salt of (R)-4-amino-3-(4-chlorophenyl)butanoic acid. The salt was analyzed under HPLC optical purity analysis conditions described below. As a result, the enantiomer excess thereof was 99.4%.

(HPLC Optical Purity Analysis Conditions)
  column: CROWNPAK CR(+) (4.6 mm×250 mm),
  mobile phase: water, the pH of which was adjusted to 2 with $HClO_4$,
  flow rate: 2.0 mL/minute,
  column temperature: 40° C., and
  detector: UV 220 nm.

Comparative Example 1

In accordance with the process described in US2009/0137819, 80.0 g of a hydrochloride salt of (R)-4-amino-3-(4-chlorophenyl)butanoic acid, the enantiomer excess of which was 99.4%, was added to 163 g of water so as to dissolve the salt in water. To the resultant solution, 0.9 g of activated carbon was added, and then the obtained slurry was stirred at about 40° C. for 1 hour. Thereafter, the mixture was filtrated at about 40° C., and the residue was washed with 73 g of water. The filtrate and the washing liquid were combined to prepare an aqueous solution of the hydrochloride salt of (R)-4-amino-3-(4-chlorophenyl)butanoic acid. An aqueous solution of sodium hydroxide was dropwise added thereto, and the concentration of the sodium hydroxide was adjusted to about 14% by weight at about 22° C. so as to adjust the pH of the mixture to 7-8. In this way, crystals were precipitated. In other words, neutralizing crystallization was performed. The mixture was filtrated to take out the crystals, and the taken-out crystals were washed with 17.4 g of water, and then dried at 50° C. under reduced pressure to yield 64.2 g of crystals of (R)-4-amino-3-(4-chlorophenyl)butanoic acid.

The resultant crystals were partially taken out, and pulverized. The pulverized crystals were then analyzed under powder X-ray diffraction analysis conditions described below. As a result, a diffraction peak was not observed within the range of a diffraction angle 2θ of 8.7 to 9.4°, within the range of a diffraction angle 2θ of 12.2 to 12.8°, nor within the range of a diffraction angle 2θ of 24.8 to 25.4°. Diffraction peaks were observed at diffraction angles 2θ of 21.0°, 26.9°, and 29.8°. In short, it was verified that the crystals yielded by the neutralizing crystallization was crystal B.

(Powder X-Ray Diffraction Analysis Conditions)
  X-ray: Cu/30 kV/15 mA,
  goniometer: goniometer, Mini Flex II
  filter: Kμ filter,
  divergent slit: 1.25°,
  light receiving slit: 0.3 mm,
  scattering slit: 1.25°,
  sampling width: 0.02°,
  scanning range: 2.00 to 40.00°,
  number of times of integration (or multiplication): 1,
  scanning speed: 2.0°/minute,
  scanning axis: 2θ/θ, and
  θ offset: 0°.

Example 1

Crystal B (16 g) yielded in Comparative Example 1 was mixed with 75 g of the filtrate yielded by the filtration when the crystals were taken out in Comparative Example 1 (the filtrate contained, as main components thereof, water, sodium hydroxide, and sodium chloride). The pH of the resultant mixture, that is, the pH of water in the mixture was from 7.5 to 7.6. This mixture was heated to about 65° C., and crystal B was stirred in water, the pH of which was from 7 to 8, for 1 hour, and then cooled to 50° C. The cooled mixture was filtrated to take out crystals. The taken-out crystals were washed with 25 g of water, and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 82%.

The crystals were analyzed under the above-mentioned HPLC optical purity analysis conditions. As a result, the enantiomer excess thereof was 99.8%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 9.3°, 12.7°, and 25.0°. In short, it was verified that the resultant crystals were crystal A.

Example 2

Crystal B (16 g) yielded in Comparative Example 1 was mixed with 74 g of the filtrate yielded by the filtration when the crystals were taken out in Comparative Example 1 (the filtrate contained, as main components thereof, water, sodium hydroxide, and sodium chloride). Thereto was added 11.5 g of 3 mol/L hydrochloric acid to yield a mixture having a pH of 3.2 to 3.3. The resultant mixture was heated to about 65° C., and crystal B was stirred in water, the pH of which was from 3 to 4, for 2 hours, and then cooled to 50° C. The cooled mixture was filtrated to take out crystals. The taken-out crystals were washed with 25 g of water, and then dried at 50° C. under reduced pressure to yield crystals of (R)-4-amino-3-(4-chlorophenyl) butanoic acid. The yield thereof from the hydrochloride salt of (R)-4-amino-3-(4-chlorophenyl)butanoic acid was 47%.

The crystals were analyzed under the above-mentioned HPLC optical purity analysis conditions. As a result, the enantiomer excess thereof was 99.9%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 9.3°, 12.7°, and 25.0°. In short, it was verified that the resultant crystals were crystal A.

Synthesis Example 5

To 120 g of water was added 60.0 g of a hydrochloride salt of (R)-4-amino-3-(4-chlorophenyl)butanoic acid, the enantiomer excess of which was 99.2%, so as to dissolve the salt in water. To the resultant solution was added 0.6 g of activated carbon, and then the slurry was stirred at about 40° C. Thereafter, the mixture was filtrated, and the residue was washed with 54 g of water. The filtrate and the washing liquid were combined with each other, and then an aqueous solution (about 14% by weight) of sodium hydroxide was dropwise added thereto at about 25° C. to adjust the pH of the mixture to 7-8. In this way, crystals were precipitated. In other words, neutralizing crystallization was performed. To the resultant mixture was added 1.7 mL of acetic acid at 25° C. to adjust the pH to 4-5. Thereafter, the mixture was filtrated to take out the crystals, and the taken-out crystals were washed with 14.8 g of water to yield 101.2 g of crystals of (R)-4-amino-3-(4-chlorophenyl)butanoic acid.

The resultant crystals were partially taken out, and (R)-4-amino-3-(4-chlorophenyl)butanoic acid was then quantitatively analyzed under HPLC analysis conditions described below. The amount of pure (R)-4-amino-3-(4-chlorophenyl) butanoic acid in the resultant crystals were 43.8 g, and the yield thereof was 85%.

(HPLC Analysis Conditions)
 column: CAPCELL PAK C8 DD (4.6 mm×150 mm, 5 μm),
 mobile phase: liquid A=0.1% solution of phosphoric acid in water, and
  liquid B=acetonitrile,
 mobile phase gradient:
  liquid B: 10% at the start→60% at 20 minutes→60% at 35 minutes→10% at 35.1 minutes→45 minutes,
 flow rate: 1 mL/minute,
 column temperature: 30° C., and
 detector: UV 210 nm.

The resultant crystals were partially taken out, dried and pulverized. The pulverized crystals were then analyzed under the above-mentioned powder X-ray diffraction analysis conditions. As a result, a diffraction peak was not observed within the range of a diffraction angle 2θ of 8.7 to 9.4°, within the range of a diffraction angle 2θ of 12.2 to 12.8°, nor within the range of a diffraction angle 2θ of 24.8 to 25.4°. Diffraction peaks were observed at diffraction angles 2θ of 21.0°, 26.9°, and 29.9°. In short, it was verified that the resultant crystals were crystal B.

Example 3

Crystal B (33 g; the amount of pure (R)-4-amino-3-(4-chlorophenyl)butanoic acid: 14.3 g) yielded in Synthesis Example 5 was mixed with 71 g of the filtrate yielded by the filtration when the crystals were taken out in Synthesis Example 5 (the filtrate contained, as main components thereof, water, acetic acid and sodium hydroxide), so as to prepare a mixture having a pH of 4 to 5. This mixture was heated at 85 to 87° C., and crystal B was stirred in water, the pH of which was from 4 to 5, for 20 minutes, and then cooled to 50° C. The cooled mixture was filtrated. The residue was washed with 25 g of water, and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 90%.

The crystals were analyzed under the above-mentioned HPLC optical purity analysis conditions. As a result, the enantiomer excess thereof was 99.3%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 8.9°, 12.3°, and 25.2°. In short, it was verified that the resultant crystals were crystal A.

Example 4

Crystal B (33 g; the amount of pure (R)-4-amino-3-(4-chlorophenyl)butanoic acid: 14.3 g) yielded in Synthesis Example 5 was mixed with 71 g of the filtrate yielded by the filtration when the crystals were taken out in Synthesis Example 5 (the filtrate contained, as main components thereof, water, acetic acid, and sodium hydroxide), so as to prepare a mixture having a pH of 4 to 5. This mixture was heated at 65 to 71° C., and crystal B was stirred in water, the pH of which was from 4 to 5, for 1 hour and 40 minutes, and then cooled to 50° C. The cooled mixture was filtrated. The residue was washed with 25 g of water, and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 89%.

The crystals were analyzed under the above-mentioned HPLC optical purity analysis conditions. As a result, the enantiomer excess thereof was 99.9%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 8.9°, 12.3°, and 25.2°. In short, it was verified that the resultant crystals were crystal A.

Example 5

Crystal B (33 g; the amount of pure (R)-4-amino-3-(4-chlorophenyl)butanoic acid: 14.3 g) yielded in Synthesis Example 5 was mixed with 71 g of the filtrate yielded by the filtration when the crystals were taken out in Synthesis Example 5 (the filtrate contained, as main components thereof, water, acetic acid, and sodium hydroxide), so as to prepare a mixture having a pH of 4 to 5. This mixture was heated at 51 to 52° C., and crystal B was stirred in water, the pH of which was from 4 to 5, for 10 hours, and then cooled to 50° C. The cooled mixture was filtrated. The residue was washed with 25 g of water, and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 85%.

The crystals were analyzed under the above-mentioned HPLC optical purity analysis conditions. As a result, the enantiomer excess thereof was 99.9%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 9.3°, 12.7°, and 25.0°. In short, it was verified that the resultant crystals were crystal A.

Example 6

To 81 g of water was added 40.0 g of a hydrochloride salt of (R)-4-amino-3-(4-chlorophenyl)butanoic acid so as to dissolve the salt in water. To the resultant solution was added 0.4 g of activated carbon, and then the slurry was stirred at about 45° C. for 40 minutes. Thereafter, the mixture was filtrated, and the residue was washed with 37 g of water. The filtrate and the washing liquid were combined with each other, and then an aqueous solution (about 14% by weight) of sodium hydroxide was dropwise added thereto at about 25° C. to adjust the pH of the mixture to 7.3. In this way, crystals were precipitated. In other words, neutralizing crystallization was performed. To the resultant mixture containing crystal B was added 0.3 mL of acetic acid at 25° C. to adjust the pH to 4.8. Thereafter, the mixture was heated, and crystal B was stirred in water having a pH of 4 to 5 at 67 to 70° C. for 1 hour. The resultant mixture was cooled to about 50° C., and then stirred for 30 minutes. The mixture was then filtrated to take out the crystals, and the taken-out crystals were washed with 61 g of water. The washed crystals were dried at 53° C. under reduced pressure to yield 30.9 g of crystals of (R)-4-amino-3-(4-chlorophenyl)butanoic acid. The yield thereof from the hydrochloride salt of (R)-4-amino-3-(4-chlorophenyl)butanoic acid was 90%.

The crystals were analyzed under the above-mentioned HPLC optical purity analysis conditions. As a result, the enantiomer excess thereof was 99.9%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 20.8 to 21.4°, within the range of a diffraction angle 2θ of 26.7 to 27.3°, nor within the range of a diffraction angle 2θ of 29.7 to 30.3°. Diffraction peaks were observed at diffraction angles 2θ of 9.3°, 12.7°, and 25.0°. In short, it was verified that the resultant crystals were crystal A.

Comparative Example 2

In accordance with the process descried in Journal of the Chemical Society, Perkin Transactions 2, 1997, pp. 763-768, 6.1 g of (R)-3-(4-chlorophenyl)glutaramide acid was mixed with sodium hydroxide (2.6 moles per mole of (R)-3-(4-chlorophenyl) glutaramide acid) in water. While the mixture was cooled in an ice bath, sodium hypochlorite (1.6 moles per mole of (R)-3-(4-chlorophenyl) glutaramide acid) was added to the mixture to adjust the pH to 11. The mixture was stirred at room temperature for 12 hours, and then 1 mol/L of hydrochloric acid was dropwise added to the reaction mixture to adjust the pH of the mixture to 7.5, thereby precipitating crystals. In other words, neutralizing crystallization was attained. The crystals were taken out by filtration, and the taken-out crystals were treated in refluxing methanol. The crystals were then filtrated, washed and dried to yield crystal I. Methanol was added to the filtrate obtained when the crystals were taken out, and then the methanol-added filtrate was treated while heated and refluxed. Thereafter, the resultant crystals were filtrated, washed and dried to yield crystal II. The yield was 23%.

Crystals I and II were each partially taken out, and pulverized. The pulverized crystals were then analyzed under the above-mentioned powder X-ray diffraction analysis conditions. As a result, a diffraction peak was not observed within the range of a diffraction angle 2θ of 8.7 to 9.4°, within the range of a diffraction angle 2θ of 12.2 to 12.8°, nor within the range of a diffraction angle 2θ of 24.8 to 25.4°. Diffraction peaks were observed at diffraction angles 2θ of 21.0°, 27.0°, and 29.9°. In short, it was verified that the resultant crystals were each crystal B.

Reference Example 1

Crystal B (16 g) yielded in Comparative Example 1 was mixed with 76 g of methanol, and the resultant mixture was heated to about 65° C. and then stirred for 20 hours. The mixture was then cooled to 50° C. The cooled mixture was filtrated to take out crystals, and the taken-out crystals were washed with 40 g of methanol and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 86%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 8.7 to 9.4°, within the range of a diffraction angle 2θ of 12.2 to 12.8°, nor within the range of a diffraction angle 2θ of 24.8 to 25.4°. Diffraction peaks were observed at diffraction angles 2θ of 21.0°, 26.9°, and 29.9°. In short, it was verified that the resultant crystals were crystal B.

Reference Example 2

Crystal B (16 g) yielded in Comparative Example 1 was mixed with 79 g of the filtrate yielded by the filtration when the crystals were taken out in Comparative Example 1 (the filtrate contained, as main components thereof, water, sodium hydroxide, and sodium chloride). Thereto was added 6.8 g of an aqueous solution (about 14% by weight) of sodium hydroxide to yield a mixture having a pH of 10. The resultant mixture was heated to about 65° C. and then crystal B was stirred in water having a pH of 10 for 24 hours. The mixture was then cooled to 50° C. The cooled mixture was filtrated to take out crystals, and the taken-out crystals were washed with 24 g of water and then dried at 50° C. under reduced pressure to yield crystals of (R)-4-amino-3-(4-chlorophenyl)butanoic acid. The yield thereof from the hydrochloride salt of (R)-4-amino-3-(4-chlorophenyl)butanoic acid was 67%.

The resultant crystals were partially taken out, and pulverized. The pulverized crystals were then analyzed under the above-mentioned powder X-ray diffraction analysis conditions. As a result, a diffraction peak was not observed within the range of a diffraction angle 2θ of 8.7 to 9.4°, within the range of a diffraction angle 2θ of 12.2 to 12.8°, nor within the range of a diffraction angle 2θ of 24.8 to 25.4°. Diffraction peaks were observed at diffraction angles 2θ of 21.0°, 27.0°, and 29.9°. In short, it was verified that the resultant crystals were crystal B.

Test Example 1

About each of crystal A yielded according to the same process in Example 1, and crystal B yielded according to the same process in Comparative Example 1, a device manufactured by SII Nano Technology Inc., EXTER 6000, was used to measure the DSC thereof under differential scanning calorie analysis conditions described below. The results are shown in Table 3.

As shown in Table 3, crystal A showed a higher endothermic peak and a higher exothermic peak than crystal B. For this reason, crystal A is far better in thermal stability than crystal B. Moreover, it is expected that crystal A is far better in storage stability than crystal B.

(Differential Scanning Calorie Analysis Conditions)
measuring temperature range: 25 to 500° C.,
temperature-raising rate: 10° C./minute,
container: air-tightly closed SUS,
sample amount: about 0.4 to 0.7 mg,
reference: α-alumina having a weight of about 0.6 mg, and
atmospheric gas flow rate: dried nitrogen, about 70 mL/minute.

TABLE 3

|  | Crystal A | Crystal B |
| --- | --- | --- |
| Endothermic peak | 203° C. | 187° C. |
| Exothermic peak | 386° C. | 349° C. |

Test Example 2

About each of crystal A yielded according to the same process in Example 1, and crystal B yielded according to the same process in Comparative Example 1, the solubility thereof in 100 g of water was measured. The results are shown in Table 4.

TABLE 4

|  | Crystal A | Crystal B |
| --- | --- | --- |
| 25° C. | 0.88 g | 1.98 g |
| 40° C. | 1.16 g | — |
| 55° C. | — | 2.59 g |
| 75° C. | 2.20 g | 2.86 g |

INDUSTRIAL APPLICABILITY

Optically active 4-amino-3-(4-chlorophenyl)butanoic acid has been developed as a raw material of medicine, or an intermediate thereof. The invention is industrially applicable as a new crystal far better in stability of this compound, and a process for producing the crystal.

The invention claimed is:

1. A crystal A of optically active 4-amino-3-(4-chlorophenyl)butanoic acid, characterized by a X-ray diffraction pattern comprising peaks at 8.9°, 18.6°, 19.2°, 21.9°, 22.8°, 23.3°, 24.6°, 25.8°, 26.4°, 27.8°, 28.9°, 30.7°, 34.8°, 37.4°, and 39.5+/−0.2° 2θ.

2. The crystal according to claim 1, wherein the optically active 4-amino-3-(4-chlorophenyl)butanoic acid is (R)-4-amino-3-(4-chlorophenyl)butanoic acid.

3. A process for producing the following crystal A, comprising a step of heating the following crystal B in water having a pH of 3 to 9:
crystal A:
a crystal of optically active 4-amino-3-(4-chlorophenyl) butanoic acid characterized by a X-ray diffraction pattern comprising peaks at 8.9°, 18.6°, 19.2°, 21.9°, 22.8°, 23.3°, 24.6°, 25.8°, 26.4°, 27.8°, 28.9°, 30.7°, 34.8°, 37.4°, and 39.5°+/−0.2° 2θ; and
crystal B:
a crystal of optically active 4-amino-3-(4-chlorophenyl) butanoic acid characterized by a X-ray diffraction pattern comprising peaks at 14.5, 18.6, 20.1, 21.0, 21.9, 22.6, 23.7, 25.6, 26.4, 27.0, 27.6, 28.6, 29.3, 29.9, 31.4, 32.0 and 33.2+/−0.2° 2θ.

4. The producing process according to claim 3, wherein the step of heating the crystal B is carried out at a temperature within the range of from 40 to 100° C.

5. The producing process according to claim 3, wherein the step of heating the crystal B is carried out at a temperature within the range of from 50 to 90° C.

6. The process according to claim 3, wherein the optically active 4-amino-3-(4-chlorophenyl)butanoic acid of crystal A and the optically active 4-amino-3-(4-chlorophenyl)butanoic acid of crystal B are (R)-4-amino-3-(4-chlorophenyl)butanoic acid, respectively.

7. The crystal of claim 1, wherein the X-ray diffraction pattern is as depicted in FIG. 1.

8. The crystal of claim 1, wherein the X-ray diffraction pattern comprises peaks at 8.9°, 12.3°, 13.2°, 15.4°, 17.4°, 18.6°, 19.2°, 21.9°, 22.8°, 23.3°, 24.6°, 25.2°, 25.8°, 26.4°, 27.8°, 28.9°, 29.6°, 30.7°, 31.2°, 32.3°, 32.9°, 34.8°, 35.8°, 36.6°, 37.4°, 38.5°, and 39.5°.

* * * * *